US00PP21484P2

(12) United States Plant Patent
Dümmen

(10) Patent No.: US PP21,484 P2
(45) Date of Patent: Nov. 16, 2010

(54) POINSETTIA PLANT NAMED 'DUEPREMIMICE'

(50) Latin Name: *Euphorbia pulcherrima Willd.*
Varietal Denomination: Duepremimice

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/586,293

(22) Filed: Sep. 18, 2009

(51) Int. Cl.
*A01H 5/00* (2006.01)

(52) U.S. Cl. ..... Plt./303

(58) Field of Classification Search ..... Plt./303
See application file for complete search history.

*Primary Examiner*—Annette H Para

(74) *Attorney, Agent, or Firm*—C. A. Whealy

(57) ABSTRACT

A new and distinct cultivar of Poinsettia plant named 'Duepremimice', characterized by its compact, upright and outwardly spreading plant habit; freely branching habit; early flowering habit; inflorescences with pale yellow and red bi-colored flower bracts; and excellent post-production longevity.

1 Drawing Sheet

Botanical designation: *Euphorbia pulcherrima* Willd.
Cultivar denomination: 'Duepremimice'.

BACKGROUND OF THE INVENTION

The present invention relates to a new and distinct cultivar of Poinsettia plant, botanically known as *Euphorbia pulcherrima* Willd., and hereinafter referred to by the name 'Duepremimice'.

The new Poinsettia plant is a naturally-occurring whole plant mutation of a proprietary selection of *Euphorbia pulcherrima* Willd. identified as code number E-16-18, not patented. The new Poinsettia was discovered and selected by the Inventor as a single flowering plant within a population of plants of the parent selection in a controlled greenhouse environment in Rheinberg, Germany on Nov. 1, 2008.

Asexual reproduction of the new Poinsettia plant by terminal vegetative cuttings in a controlled greenhouse environment in Rheinberg, Germany since June, 2009, has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Duepremimice'. These characteristics in combination distinguish 'Duepremimice' as a new and distinct cultivar of Poinsettia:

1. Compact, upright and outwardly spreading plant habit.
2. Freely branching habit.
3. Early flowering habit.
4. Inflorescences with pale yellow and red bi-colored flower bracts.
5. Excellent post-production longevity.

Plants of the new Poinsettia differ primarily from plants of the parent selection in flower bract coloration as plants of the parent selection have red-colored flower bracts.

Plants of the new Poinsettia differ primarily from plants of 'Duepremimpol', disclosed in a U.S. Plant patent application No. 12/586,299, in flower bract color as plants of 'Duepremimpol' have pale yellow-colored flower bracts.

Plants of the new Poinsettia can also be compared to plants of *Euphorbia pulcherrima* Willd. 'Ice Punch', disclosed in U.S. Plant Pat. No. 19,504. In side-by-side comparisons conducted in Rheinberg, Germany, plants of the new Poinsettia differed from plants of 'Ice Punch' in the following characteristics:

1. Plants of the new Poinsettia were more compact than plants of 'Ice Punch'.
2. Plants of the new Poinsettia were more freely branching than plants of 'Ice Punch'.
3. Plants of the new Poinsettia had shorter internodes than plants of 'Ice Punch'.
4. Plants of the new Poinsettia flowered earlier than plants of 'Ice Punch'.

BRIEF DESCRIPTION OF THE PHOTOGRAPH

The accompanying photograph illustrates the overall appearance of the new Poinsettia plant. The photograph shows the colors as true as it is reasonably possible to obtain in colored reproductions of this type. Colors in the photograph may differ slightly from the color values cited in the detailed botanical description which accurately describe the colors of the new Poinsettia plant. The photograph comprises a side perspective view of a typical flowering plant of 'Duepremimice' grown in a container.

DETAILED BOTANICAL DESCRIPTION

The aforementioned photograph and following observations and measurements describe plants grown in Rheinberg, Germany during the winter in a glass-covered greenhouse and under conditions and practices which approximate those generally used in commercial Poinsettia production. During the production of the plants, day and night temperatures averaged 22° C. and light levels were about 4,500 lux. Measurements and numerical values represent averages for typical flowering plants. Single plants were grown in 13-cm containers and were pinched one time five weeks after planting the cuttings. Plants were 16 weeks from planting when the photograph and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'Duepremimice'.

Parentage: Naturally-occurring whole plant mutation of a proprietary selection of *Euphorbia pulcherrima* Willd. identified as code number E-16-18, not patented.

Propagation:

*Type.*—Terminal vegetative cuttings.

*Time to initiate roots, summer.*—About nine days at 22° C.

*Time to initiate roots, winter.*—About 13 days at 22° C.

*Time to produce a rooted young plant, summer.*—About three weeks at 22° C.

*Time to produce a rooted young plant, winter.*—About four weeks at 22° C.

*Root description.*—Fibrous, fleshy, medium in thickness; white in color.

*Rooting habit.*—Freely branching; dense.

Plant description:

*Plant habit and form.*—Compact, upright and outwardly spreading plant habit; inverted triangle; inflorescences positioned above the foliar plane; moderately vigorous growth habit.

*Plant height.*—About 19 cm.

*Plant diameter or spread.*—About 30 cm.

*Lateral branch description.*—Quantity: Freely branching habit, about six lateral branches develop after pinching. Length: About 15 cm. Diameter: About 6 mm. Internode length: About 1.2 cm. Strength: Strong. Texture: Smooth, glabrous. Color: Close to 137A.

*Foliage description.*—Arrangement: Alternate, simple. Length: About 10.4 cm. Width: About 7.1 cm. Shape: Ovate. Apex: Apiculate. Base: Obtuse. Margin: Entire with dentate lobing. Venation pattern: Pinnate. Texture, upper and lower surfaces: Smooth, glabrous. Color: Developing leaves, upper surface: Close to 141A. Developing leaves, lower surface: Close to 138A. Fully expanded leaves, upper surface: Close to 139A; venation, close to 146C. Fully expanded leaves, lower surface: Close to 138A; venation, close to 144B. Petiole: Length: About 4.7 cm. Diameter: About 2.6 mm. Texture, upper and lower surfaces: Smooth, glabrous. Color, upper and lower surfaces: Close to 144B tinted with close to 59A.

Inflorescence description:

*Inflorescence type and habit.*—Inflorescences are compound corymbs of cyathia with colored flower bracts subtending the cyathia; one inflorescence per lateral branch; inflorescences positioned above the foliar plane.

*Fragrance.*—None detected.

*Natural flowering season.*—Autumn/winter; inflorescence initiation and development is induced under long nyctoperiod conditions; early flowering, response time is about eight weeks.

*Post-production longevity.*—Excellent post-production longevity; plants of the new Poinsettia maintain good substance and bract color for about eight weeks under interior conditions and about twelve weeks under greenhouse conditions; inflorescences persistent.

*Inflorescence size.*—Diameter: About 20 cm. Height (depth): About 3 cm.

*Flower bracts.*—Quantity per inflorescence: About 15. Length: About 9.1 cm. Width: About 6.6 cm. Shape: Ovate; slightly lobed. Apex: Apiculate. Base: Obtuse. Margin: Entire with dentate lobing. Texture, upper and lower surfaces: Glabrous; rugose. Venation pattern: Pinnate. Color: Developing bracts, upper surface: Center, close to 8C; towards the margins, close to 46A. Developing bracts, lower surface: Close to 46A. Fully expanded bracts, upper surface: Center, close to 8C; towards the margins, close to 46B; outer color becoming closer to 46C with development. Fully expanded bracts, lower surface: Close to 46D. Venation, upper and lower surfaces: Similar to flower bract color. Bract petiole: Length: About 1.9 cm. Diameter: About 2 mm. Texture, upper and lower surfaces: Smooth, glabrous. Color, upper and lower surfaces: Close to 144B.

*Cyathia.*—Quantity per corymb: About ten. Diameter of cyathia cluster: About 2.5 cm. Length: About 8 mm. Width: About 6 mm. Shape: Ovoid. Color, immature: Close to 144B. Color, mature: Close to 144A. Nectaries: Quantity per cyathium: One or two. Diameter: About 6 mm. Color: Close to 14B.

*Peduncles.*—Length: About 3 mm. Diameter: About 2 mm. Strength: Strong. Texture: Smooth, glabrous. Color: Close to 144B.

*Reproductive organs.*—Stamens: Quantity per cyathium: About 20. Anther shape: Oval. Anther length: About 0.5 mm. Anther color: Close to 26B. Amount of pollen: Abundant. Pollen color: Close to 14B. Pistils: Quantity per cyathium: One. Pistil length: About 1 cm. Style length: About 2 mm. Style color: Close to 53A. Stigma shape: Crested. Stigma color: Close to 144B. Ovary color: Close to 144B. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 12° C. to about 40° C.

It is claimed:

1. A new and distinct Poinsettia plant named 'Duepremimice' as illustrated and described.

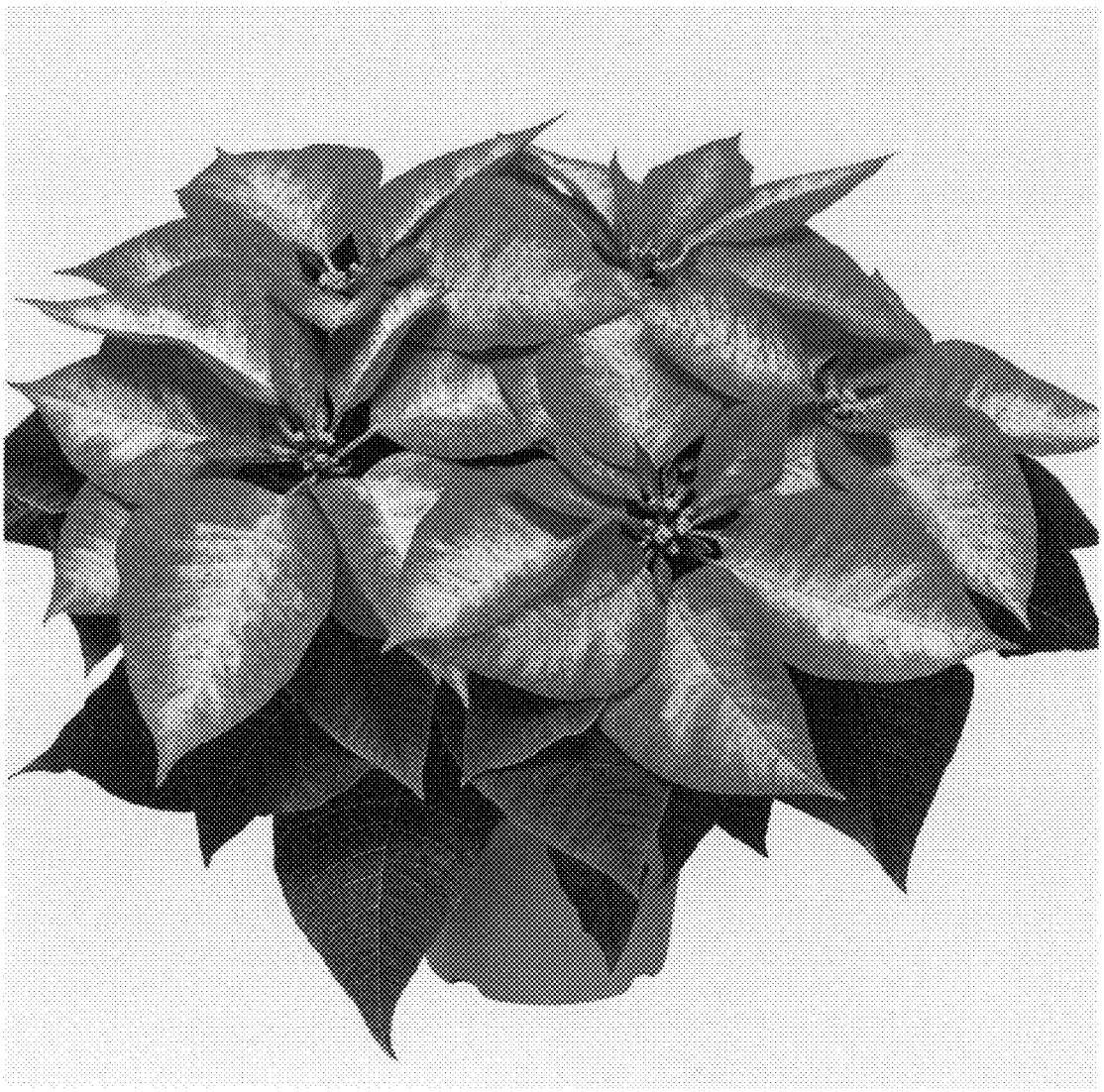

* * * * *